US006866859B2

(12) United States Patent
Trogolo et al.

(10) Patent No.: US 6,866,859 B2
(45) Date of Patent: Mar. 15, 2005

(54) BI-LAMINAR, HYALURONAN COATINGS WITH SILVER-BASED ANTI-MICROBIAL PROPERTIES

(75) Inventors: Jeffrey A. Trogolo, Boston, MA (US); James B. Johnston, Ambler, PA (US); Elizabeth A. Pastecki, Malden, MA (US); Elizabeth Pervin, Philadelphia, PA (US); Amy Stahl, New Milford, CT (US); Mark Hyman, Woburn, MA (US)

(73) Assignees: Biocoat Incorporated, Fort Washington, PA (US); AgION Technologies, LLC, Wakefield, MA (US)

( * ) Notice: Subject to any disclaimer, the term of this patent is extended or adjusted under 35 U.S.C. 154(b) by 333 days.

(21) Appl. No.: 09/940,849

(22) Filed: Aug. 29, 2001

(65) Prior Publication Data

US 2002/0068093 A1 Jun. 6, 2002

Related U.S. Application Data

(60) Provisional application No. 60/229,149, filed on Aug. 30, 2000, now abandoned.

(51) Int. Cl.$^7$ ................................................. A61F 2/02
(52) U.S. Cl. ....................................................... 424/423
(58) Field of Search ........................................ 424/423

(56) References Cited

U.S. PATENT DOCUMENTS

| | | |
|---|---|---|
| 4,657,820 A | 4/1987 | Halpern et al. |
| 4,663,233 A | 5/1987 | Beavers |
| 4,722,867 A | 2/1988 | Halpern et al. |
| 4,775,585 A | 10/1988 | Hagiwara et al. |
| 4,801,475 A | 1/1989 | Halpern et al. |
| 4,906,464 A | 3/1990 | Yamamoto et al. |
| 4,911,898 A | 3/1990 | Hagiwara et al. |
| 4,911,899 A | 3/1990 | Hagiwara et al. |
| 4,923,450 A | 5/1990 | Maeda et al. |
| 4,938,955 A | 7/1990 | Niira et al. |
| 4,938,958 A | 7/1990 | Niira et al. |
| 4,959,074 A | 9/1990 | Halpern et al. |
| 5,009,898 A | 4/1991 | Sakuma et al. |
| 5,019,096 A | 5/1991 | Fox, Jr. et al. |
| 5,023,114 A | 6/1991 | Halpern et al. |
| 5,037,677 A | 8/1991 | Halpern et al. |
| 5,102,401 A | 4/1992 | Lambert et al. |
| 5,157,005 A | 10/1992 | Suppiah |
| 5,180,585 A | 1/1993 | Jacobson et al. |
| 5,244,667 A | 9/1993 | Hagiwara et al. |
| 5,264,250 A | 11/1993 | Steele et al. |
| 5,296,238 A | 3/1994 | Sugiura et al. |
| 5,305,827 A | 4/1994 | Steele et al. |
| 5,405,644 A | 4/1995 | Ohsumi et al. |
| 5,441,717 A | 8/1995 | Ohsumi et al. |
| 5,474,797 A | 12/1995 | Sioshansi et al. |
| 5,492,763 A | 2/1996 | Barry et al. |
| 5,509,899 A | 4/1996 | Fan et al. |
| 5,520,664 A | 5/1996 | Bricault et al. |
| 5,556,699 A | 9/1996 | Niira et al. |
| 5,562,872 A | 10/1996 | Watanabe |
| 5,697,203 A | 12/1997 | Niwa |
| 5,698,229 A | 12/1997 | Ohsumi et al. |
| 5,714,430 A | 2/1998 | Gehrer et al. |
| 5,714,445 A | 2/1998 | Trinh et al. |
| 5,723,110 A | 3/1998 | Yamamoto et al. |
| 5,753,251 A | 5/1998 | Burrell et al. |
| 5,770,255 A | 6/1998 | Burrell et al. |
| 5,783,570 A | 7/1998 | Yokota et al. |
| 5,789,571 A | 8/1998 | Beavers et al. |
| 5,800,412 A | 9/1998 | Zhang et al. |
| 5,840,046 A | 11/1998 | Deem |
| 6,013,275 A | 1/2000 | Konagaya et al. |
| 6,042,876 A | 3/2000 | Deem |
| 6,187,369 B1 | 2/2001 | Beavers |

FOREIGN PATENT DOCUMENTS

WO   WO 00/30697   * 6/2000

OTHER PUBLICATIONS

Patent Abstracts of Japan, Publication No. 05154174, May 22, 1993, Kanebo Ltd.
Abstract of Japanese Patent Document No. JP9100205, Aug. 1, 1995.
Abstract of Japanese Patent Document No. JP10152579, Jun. 9, 1998.
"Anti–Infective Medical Device Strategies", Chinn et al. Surfaces in Biomaterials Foundation, 1998, p. 105–110.
"The Patho Physiology and Management of Device Related Infections", Khoury, Surfaces in Biomaterials Fd., 1998, p. 99–104.
"Hyaluronan–Modified Surfaces for Medical Devices", Hoekstra, Medical Device & Diagnostic Industry, Feb. 1999.
"Evaluation of Interfacial Properties of Hyaluronan, etc." Cassinelli et al, J. Biomater. Sci. Polymer Edn, vol. 11, No. 9.

* cited by examiner

Primary Examiner—Carlos A. Azpuru
(74) Attorney, Agent, or Firm—William H. Eilberg

(57) ABSTRACT

An article including a surface having a coating thereon, in which the coating includes a base coat, firmly adhered to the surface, and a hydrophilic, biocompatible top-coat. An antibiotic ceramic component is dispersed in one or both of the base coat and top-coat. Preferably, the ceramic component is dispersed in the base coat. In a preferred embodiment, the ceramic component is a zeolite with silver ions exchanged onto internal acidic sites of the zeolite, and the top-coat includes a polysaccharide, such as hyaluronan. The zeolite is highly effective in imparting anti-microbial character to the coating.

20 Claims, No Drawings

BI-LAMINAR, HYALURONAN COATINGS WITH SILVER-BASED ANTI-MICROBIAL PROPERTIES

CROSS-REFERENCE TO PRIOR APPLICATION

This application corresponds to U.S. Provisional Patent Application Ser. No. 60/229,149, filed Aug. 30, 2000.

BACKGROUND OF THE INVENTION

The present invention generally relates to anti-microbial coatings and surfaces.

Silver ion is one example of the relatively few antiseptic materials which are tolerated internally by humans at concentrations that are effective to kill microbes. Among antiseptic metal ions, silver is one of the best known. Silver is particularly useful because it is not substantially absorbed into the body. With an exceedingly long history of use, water-soluble silver salts have been used as antiseptics for hundreds of years, and are perhaps best known for disinfecting the eyes of newborn infants, thus preventing blindness. Other antiseptic metal ions include copper, zinc, mercury, tin, lead, bismuth, cadmium, chromium, and thallium. But the latter ions are less preferred than silver for internal use. The afore-mentioned metal ions are believed to exert their effects by disrupting respiration and electron transport systems upon absorption into bacterial or fungal cells.

Unless stated otherwise, the term "silver", when used alone in this specification, means silver ion.

A preferred inorganic antimicrobial agent is an antibiotic zeolite. Suitable zeolites are disclosed in U.S. Pat. No. 4,938,955, the disclosure of which is incorporated by reference herein. Antibiotic zeolites have been prepared by replacing all or part of the ion-exchangeable ions in zeolite with ammonium ions and antibiotic metal ions, as described in U.S. Pat. Nos. 4,938,958 and 4,911,898, the disclosures of which are incorporated by reference herein. Such zeolites have been incorporated into resins, and used to make various products such as refrigerators, dishwashers, rice cookers, plastic film, chopping boards, vacuum bottles, plastic pails, garbage containers, flooring, wall paper, cloth, paint, napkins, plastic automobile parts, catheters, bicycles, pens, toys, sand, and concrete. The resins incorporating the zeolites, and the uses mentioned above, are described in one or more of the above-cited patents, and/or in U.S. Pat. Nos. 4,906,464, 4,775,585, 5,714,445, 5,697,203, 5,562,872, 5,180,585, 5,714,430, and 5,102,401, the disclosures of all of which are incorporated by reference herein. Other patents relevant to zeolites include U.S. Pat. Nos. 5,556,699, 4,911, 899, and 4,923,450, the disclosures of which are also incorporated by reference herein.

Antibiotic ceramic particles useful with the present invention include zeolites, hydroxy apatite, zirconium phosphates, and other ion-exchange ceramics. Zeolites are preferred, and are described in the preferred embodiments set forth below. Hydroxy apatite particles containing antimicrobial metals are described in U.S. Pat. No. 5,009,898, the disclosure of which is incorporated by reference herein. Zirconium phosphates containing antimicrobial metals are described in U.S. Pat. Nos. 5,296,238, 5,441,717, and 5,405,644, the disclosures of which are also incorporated by reference herein.

Either natural zeolites or synthetic zeolites can be used to make the antibiotic zeolites used in the present invention. Zeolite is an aluminosilicate having a three-dimensional skeletal structure that is represented by the formula:

$$XM_2/nO\text{—}Al_2O_3\text{—}YSiO_2\text{—}ZH_2O$$

where M represents an ion-exchangeable ion, generally a monovalent or divalent metal ion, n represents the atomic valency of the metal ion, X and Y represent coefficients of metal oxide and silica respectively, and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite, and erionite. The present invention is not restricted to use of these specific zeolites.

The ion-exchange capacities of these zeolites are as follows: A-type zeolite=7 meq/g; X-type zeolite=6.4 meq/g; Y-type zeolite=5 meq/g; T-type zeolite=3.4 meq/g; sodalite= 11.5 meq/g; mordenite=2.6 meq/g; analcite=5 meq/g; clinoptilolite=2.6 meq/g; chabazite=5 meq/g; and erionite= 3.8 meq/g. These ion-exchange capacities are sufficient for the zeolites to undergo ion-exchange with ammonium and antibiotic metal ions.

The specific surface area of preferred zeolite particles is preferably at least 150 m$^2$/g (anhydrous zeolite as standard) and the SiO$_2$/Al$_2$O$_3$ mol ratio in the zeolite composition is preferably less than 14, more preferably less than 11.

The antibiotic metal ions used in the antibiotic zeolites should be retained on the zeolite particles through an ion-exchange reaction. Antibiotic metal ions which are adsorbed or attached without an ion-exchange reaction exhibit a decreased bactericidal effect and their antibiotic effect is not long-lasting. Nevertheless, it is advantageous for imparting quick antimicrobial action to maintain a sufficient amount of surface adsorbed metal ion.

During the ion-exchange process, if the concentration of metal ions in the vicinity of the zeolite surface is high, there is a tendency for the antimicrobial metal ions (cations) to be converted into their oxides, hydroxides, basic salts, etc., which deposit in the micropores or on the surfaces of the zeolite. This deposition may adversely affect the bactericidal properties of the ion-exchanged zeolite.

In an embodiment of the antibiotic zeolites, a relatively low degree of ion exchange is employed to obtain superior bactericidal properties. It is believed to be required that at least a portion of the zeolite particles retain metal ions having bactericidal properties at ion-exchangeable sites of the zeolite in an amount less than the ion-exchange saturation capacity of the zeolite. In one embodiment, the zeolite employed in the present invention retains antimicrobial metal ions in an amount up to 41% of the theoretical ion-exchange capacity of the zeolite. Such ion-exchanged zeolite with a relatively low degree of ion-exchange may be prepared by performing ion-exchange using a metal ion solution having a low concentration as compared with solutions conventionally used for ion exchange.

The antibiotic metal ion is preferably present in the range of from about 0.1 to 20% (by weight) of the zeolite. In one embodiment, the zeolite contains from 0.1 to 20% (by weight) of silver ions and from 0.1 to 20% (by weight) of copper or zinc ions. Although ammonium ion can be contained in the zeolite at a concentration of about 20% or less (by weight) of the zeolite, it is desirable to limit the content of the ammonium ions to from 0.5 to 15% (by weight), preferably 1.5 to 5%. The percent by weight described herein is determined for materials dried at temperatures such as 110° C., 250° C. or 550° C. as this is the temperature employed for the preferred post-manufacturing drying process.

A preferred antibiotic zeolite is type A zeolite containing either a combination of ion-exchanged silver, zinc, and ammonium or silver and ammonium. One such zeolite is manufactured by Shinegawa, Inc., under the product number AW-10N and consists of 0.6% (by weight) of silver ion-exchanged in Type A zeolite particles having a diameter of about 2.5 microns. Another formulation, sold under the product number AJ-10N, consists of about 2% (by weight) silver ion-exchanged in Type A zeolite particles having a diameter of about 2.5 microns. Another formulation, sold under the product number AW-80, contains 0.6% (by weight) of silver ion-exchanged in Type A zeolite particles having a diameter of about 1.0 microns. Another formulation, sold under the product number AJ-80N, consists of about 2% (by weight) silver ion-exchanged in Type A zeolite particles having a diameter of about 1.0 microns. These zeolites preferably contain between about 0.5% and 2.5%, by weight, of ion-exchanged ammonium.

The zeolites are often obtained in master batches of low density polyethylene, polypropylene, or polystyrene, containing 20% (by weight) of the zeolite.

The antibiotic properties of the antibiotic zeolite particles of the invention may be assayed while in aqueous formulations using conventional assay techniques, including, for example, determining the minimum growth inhibitory concentration (MIC) with respect to a variety of bacteria, eumycetes, and yeast. In such a test, one may use any of the following bacteria: *Bacillus cereus varmycoides, Escherichia coli, Pseudomonas aeruginosa, Staphylococcus aureus, Streptococcus faecalis, Aspergillus niger, Aureobasidium pullulans, Chaetomium globosum, Gliocladium virens, Penicillum funiculosum, Candida albicans,* and *Saccharomyces cerevisiae.*

The assay for determining MIC can be carried out by smearing a solution containing bacteria for inoculation onto a plate culture medium to which a test sample of the encapsulated antibiotic zeolite particles is added in a particular concentration, followed by incubation and culturing of the plate. The MIC is defined as a minimum concentration thereof required for inhibiting the growth of each bacteria.

A number of strategies have been used to develop anti-infective surfaces for medical devices. Various approaches are described in J. A. Chinn, M. A. Moore, G. Cook and J. W. Costerton, "Anti-infective medical device strategies": Surfaces in Biomaterials Symposium, 1998, pp. 105–109, and in A. E. Khoury, "The pathophysiology and management of device related infections": Surfaces in Biomaterials Symposium, 1998, pp. 99–103.

Among the most promising techniques are those that combine different mechanisms of activity, such as the use of materials inherently resistant to bacterial attachment, and the inclusion of anti-microbial agents in the structure or device surface. It is an object of the invention to provide such an advantageous anti-infective coating by combining an inherent resistance to microbial attachment with an antiseptic activity.

Medical devices coated with a hyaluronate surface layer are well known to exhibit a marked reduction or absence of cellular attachment and fouling by bacteria, as for example is described in D. Hoekstra, "Hyaluronan-modified surfaces for medical devices": Medical Device and Diagnostic Industry", February 1999, and "Evaluation of interfacial properties of hyaluronan coated poly(methylmethacrylate) intraocular lenses", Journal of Biomaterials Science, Polymer Edition, vol. 11, No. 9, pp. 961–978 (2000). These hyaluronate coatings also confer a high lubricity to the device surface. Hyaluronate is a negatively-charged mucopolysaccharide, present in virtually all animal life forms, that also confers high lubricity when used to coat medical devices. It nonetheless has proved difficult to modify these coatings to obtain effective, sustained anti-microbial activity without interfering with the coating chemistry itself or without modifying the properties of the final, cured hyaluronate coating. Silver ion has been particularly difficult to incorporate into hyaluronan coatings.

Examples of patents showing medical devices, and other devices, having a biocompatible coating, are U.S. Pat. Nos. 4,657,820, 4,663,233, 4,722,867, 4,801,475, 4,959,074, 5,023,114, 5,037,677, 5,789,571, 5,840,046, 6,042,876, and 6,187,369, the disclosures of which are incorporated by reference herein.

For example, the family of bi-laminar, biocompatible coatings that is commercially available under the trademark HYDAK (HYDAK is a trademark of Biocoat Incorporated, of Ft. Washington, Pa.) provides several different acrylic base coat polymers that provide adhesion to the substrate, together with a topcoat of sodium hyaluronate that is covalently grafted to the base coat. When simple, broad-spectrum anti-microbial agents like silver salts are included in the coating solutions, the silver ion interferes with the formation of the base coat film itself, as well as binding to the hyaluronate carboxylate and modifying the lubricity of the coated surface.

Nonetheless, if silver ion is exchanged onto the negatively charged surface of a hyaluronate coating, this antiseptic silver will be released into the bodily fluids upon contact with them. The silver store is rapidly exhausted, however. Thus, it is an object of the invention to provide an antiseptic silver-based coating with a more sustained release of silver that prolongs the effectiveness of the antiseptic activity.

Antibiotics added to a coated medical device, for example, by soaking the device in an antibiotic solution just before insertion into the body, are released rapidly and lost from the vicinity of the device in a matter of hours. This transient antibiotic presence may cause an immediate reduction of contaminating microbes in the vicinity of the device insertion, but the benefit is usually lost in hours, well before the withdrawal of typical coated medical devices such as urinary or central venous catheters. Any bacteria that survive this initial antibiotic release are then able to grow and cause harm. Moreover, bacteria or other pathogens often exhibit resistance to antibiotics, in contrast to antiseptics.

It therefore would be a significant advance in the art to provide a means and method for incorporating a source of anti-microbial silver ion in a bi-laminar, biocompatible coating composition of the above-described type, without the aforementioned adverse effects on base coat formation and surface lubricity.

SUMMARY OF THE INVENTION

In one embodiment, the present invention comprises an article having a surface, the surface having a bilaminar coating. The bilaminar coating includes a first layer, or base coat, which adheres firmly to the surface of the article, and a second layer, or top-coat, which is chemically joined to the base coat. The top-coat is made of a material that is hydrophilic, lubricious, and biocompatible. Preferably, the top-coat comprises a polysaccharide, such as hyaluronan. Dispersed within one or both of the base coat and top-coat is an antibiotic ceramic component, preferably a zeolite material, and more preferably, a zeolite material with silver ions ion-exchanged thereon.

In the preferred embodiment, the antibiotic ceramic component is present in the base coat, where it is likely to provide more prolonged and sustained release of antibiotic material.

The invention also includes a method of providing an object with antibiotic properties. The method includes forming a bilaminar coating on the object, the coating having the properties described above, and dispersing an antibiotic ceramic component within at least one layer of the coating. In the more preferred embodiment, the ceramic component is dispersed in the base coat. As described above, it is preferred that the ceramic component comprise a zeolite, and, more preferably, a zeolite component having silver ions ion-exchanged thereon.

The invention therefore has the primary object of imparting anti-microbial properties to articles having biocompatible coatings.

The invention has the further object of improving the safety of medical devices that are inserted into the body, by imparting antimicrobial properties to the surfaces of such devices.

The invention has the further object of providing an article having a hydrophilic, lubricious, and biocompatible coating, wherein the surface of the article also has antimicrobial properties.

The invention has the further object of providing an article as described above, wherein the article retains its antimicrobial properties for an extended period of time.

The invention has the further object of providing a method of imparting antimicrobial properties to an article which is intended to be inserted into the body.

The reader skilled in the art will recognize other objects and advantages of the present invention, from a reading of the following detailed description of the invention and the appended claims.

DETAILED DESCRIPTION OF THE INVENTION

The present invention is based on the surprising and unexpected discovery that zeolites with silver ions exchanged onto internal acidic sites of the zeolite are highly efficacious in imparting anti-microbial character to hyaluronan coatings and other polysaccharide coatings.

The coating system comprising a bi-laminar, biocompatible, lubricious coating including a base coat and a top-coat, and containing a silver zeolite as a source of broad spectrum anti-microbial ions, provides a highly useful coating for device structures and surfaces. Illustrative articles that are amenable to coating include, without limitation, medical devices such as catheters, stents, medical grafts, artificial implants, orthopedic devices, etc., as well as consumer products such as contact lenses, drinking containers, apparel articles, place mats, furniture, telecommunications and computational equipment, etc.

The base coat in the aforementioned bi-laminar biocompatible lubricious coating can be of any suitable type, including for example acrylic copolymers as well as other polymeric and copolymers, and other film-forming materials, as will be appreciated by those skilled in the art, and readily determinable without undue experimentation for a given end use application of the coating system.

The acrylic copolymer is a preferred material for various applications, and provides excellent adhesion to metal or polymeric wires or other substrates such as polymeric catheters, etc. The base coat in such bi-laminar biocompatible lubricious coating provides reactive chemical groups for grafting the biocompatible topcoat to the base coat.

The top-coat in one preferred embodiment comprises hyaluronan, a glycosaminoglycan material found in all mamalian cells, provide a biocompatible coating system. Such hyaluronan topcoat make the coated surface extremely slippery or lubricious in character, when wetted with aqueous fluids, and the top-coat is fully compatible in in vivo usage and corporeal contact. There are many other desirable top-coat materials including glycosaminoglycans and mucopolysaccharides such as chondroitin sulfate and heparin, the latter being able to confer desirable anti-thrombogenic character to a coated surface.

The silver zeolite is usefully employed in any suitable form, e.g., in a powder (e.g., in 1–4 microns diameter particles) or slurry form. The zeolite is a 100%. inorganic carrier and the silver ions therein are released through ion exchange in the use environment. The zeolite is a cation exchanger that binds silver ions. In the absence of a mobile counterion, the silver is not released, but in a use environment such as blood or other physiological fluid, containing mobile ions such as sodium ions, calcium ions, potassium ions, etc., and a mobile counterion for the silver ion such as chloride, phosphate or bicarbonate ion, the silver ions are released from the zeolite by ion exchange.

The ion-exchange type antimicrobial agents of the present invention all have a ceramic or ceramic-like support with passages within and throughout the support. In the case of zeolites, the passages are three-dimensional. In the case of zirconium phosphate, they are two-dimensional. In essence, the former is more sponge-like whereas the latter looks more like an "Oreo" cookie, wherein the passages go through the filling but not through the cookie. The supports have incorporated into them various anionic sites to which pendant cations are bound. Most often, these are Na+. To render the materials antimicrobial, an ion-exchange is conducted in a silver ionic solution whereby all or a portion of the Na+ cations (or other cations) are exchanged for the silver cations. Because of the large amount of Ag+ in the support, each individual support particle serves as a large reservoir for Ag+ ions, thus providing the long-term viability of the antimicrobial. The latter compares to the use of metal salts or organic antimicrobials which have no concentrated reservoir, and which quickly deplete.

In hyaluronan coatings containing the silver zeolite, good coating film properties are maintained, including lack of adverse effect of the silver active ingredient in the silver-containing zeolite, with respect to viscosity and coating chemistry and the process of coating film curing.

The silver zeolite is an effective anti-microbial agent in hyaluronan coatings and other polysaccharide coatings.

The coating composition containing the silver zeolite therefore achieves a substantial advance in the art, over prior art coatings containing silver salts, free silver or other forms of silver which compromise the film formation and the lubricity, durability, and biocompatibility of the hyaluronan or other mucopolysaccharide coating system.

By contrast, the coating compositions of the present invention provide a silver delivery system for biocompatible hyaluronan coatings, in which an inorganic, silver-based antimicrobial is incorporated in the hyaluronan coating without loss or deterioration of the excellent lubricity, durability, and biocompatibility inherent to such hyaluronan coatings.

The features of the invention are more fully appreciated with respect to the following discussion and non-limiting examples.

EXAMPLE 1

The purpose of this Example is to show the effect of silver ion, silver salts, and silver zeolite on the HYDAK coatings mentioned above.

A HYDAK G23 coating solution, obtained from Biocoat Incorporated, was formulated by mixing 100 g HYDAK G23 stock acrylic polymer solution (30% solids) with 5.8 g Desmodur N75 trifunctional isocyanate cross-linking agent (obtained from Bayer) and 124 g propyleneglycol methyl ether acetate solvent (PMA), available from Aldrich Chemical and other suppliers). This base coat coating solution was applied to polymethylmethacrylate test panels as a layer nominally 0.003-in. deep, with a coating knife, and the coat was cured for 40 min in a 60° C. oven. In this specification, the abbreviation "Des N" means Desmodur N75 defined above.

The top-coat coating solution contained 0.60% sodium hyaluronate (obtained from Lifecore Biomedical) plus 0.10% Triton CF10 surfactant (obtained from Union Carbide) and applying a nominally 0.006-in. deep layer by coating knife onto the cured base coat. The panels were cured for 16 h at 60° C. After curing, the panels were washed by soaking for 30 min. in deionized water. This was the basic coating procedure used for all the solution polymer-based coatings on test panels.

The influence of silver ion was tested by adding silver (I) oxide, silver acetate (obtained from Aldrich Chemical) or silver zeolite (obtained from AgION Technologies, AK10D grade, in the form of a dry powder, 2–3 microns average particle size) to the base or the top-coat coating solutions. To add silver compounds to the base coat coating solution, the desired weight of silver salt or silver zeolite was suspended in a portion of the PMA solvent used to formulate the base coat coating solution, and this suspension was mixed with the other components of the formulation. For the top-coat, the desired weight of silver salt was added directly to the coating solution and mixed with a paddle bladed mixer except that silver zeolite in the top-coat was added from a stabilized 20% silver zeolite commercial slurry, (from AgION Technologies, product number AK10N-20W) rather than the dry powder.

The resulting cured and washed coatings were examined for finger feel lubricity and for durability in a Gardner abrader. Table 1 shows the results:

TABLE 1

| Configuration | Lubricity | Abrasion Failure |
| --- | --- | --- |
| $Ag_2O$ in top-coat solution (2 panels -- 0.2% and 0.6% of coat solution, equal to 11% or 50% of solids) | Not lubricious | 50,000 cycles |
| $Ag_2O$ in basecoat solution (2 panels -- 1% and 6% of coat solution, equal to 6% and 40% of solids) | Lubricious | 200,000 cycles |
| AgAc in basecoat (1% of solution, 6% of solids) | Lubricious | 100,000 cycles |
| Silver zeolite in top-coat (64% of solids) | Lubricious | >500,000 cycles |
| Silver zeolite in basecoat (30% of solids) | Lubricious | >500,000 cycles |
| Control, no silver added | Lubricious | >500,000 cycles |

Panel coatings amended with 1% silver acetate or 1% or 6% silver oxide were fragile, surviving less than 200,000 cycles in the abrasion tester. Moreover, panels with the highest silver oxide levels were noticeably less lubricious than controls. By contrast, the control panels without silver and all the formulations containing silver zeolite were robust, surviving over 500,000 cycles in the abrader without loss of hydrophilic character or lubricity.

EXAMPLE 2

This Example contains two parts, and deals with the release of silver from silver zeolite-acrylic-polysaccharide coatings:

Part One

A series of samples were prepared by coating ethyl vinyl acetate catheter tubing, 1.5 mm. nominal diameter (Microline brand, available from Cole-Parmer). In all cases, the tubing was cleaned by wiping five times with a lint-free pad wetted with 2-propanol and dried at 60° C. for 2 hours before coating. The samples were coated with various Biocoat bilaminar coatings also containing various AgION silver zeolites. For this Example, all coatings were applied by dipping the tubing into the coating solution and withdrawing at a controlled rate. For samples A-D, the base coat was withdrawn at 0.22 in/sec and the top-coat at 2.0 in/sec. For all other examples, both base and top-coat were withdrawn at 0.20 in/sec. Curing conditions and the nature and amount of the silver zeolite are specified for each coating. Cured samples were assayed for the release of silver ion as described below.

For samples A–D, the unamended base coat coating solution was prepared by mixing 5.76 g HYDAK G23 (30% solids), 6.34 g PMA and 0.33 g Des N for 30 min using a flat-bladed mixing paddle. The unamended top-coat was an aqueous solution containing 0.60% sodium hyaluronate, 0.10% Triton CF10 and 0.60% triethylene glycol (Aldrich Chemical). Base coats were cured at 60° C. for 40 min and topcoats were cured for 12 hours at 60° C. Top-coats were applied less than 2 hours after completion of base coat curing, and top-coat curing was begun immediately after withdrawal of the tubing from the coating bath.

Individual samples A–D were prepared by modifications of this basic coating scheme as indicated in Table 2.

TABLE 2

Preparation of Samples A–D

| Sample | Base Coat | Top-coat |
| --- | --- | --- |
| A | To unamended base coat, add 1.93 g of a slurry of AgION zeolite AK10D (4.9% silver) made by mixing 1.00 g zeolite powder with 8.85 g acetone. | Use unamended top-coat |
| B | Use unamended base coat | To unamended topcoat, 46.0 g, add 4.67 g AgION AK10N-SW20 (20% aqueous suspension of zeolite, 5% silver) and 5.52 g water. |
| C | Same as for A | Same as for B |
| D | Same as for A, but use AgION zeolite AL85H (10.5% silver) in place of AK10D. | Use unamended top-coat |

To assess the release of silver ion from the zeolite in these coatings, 1.0-in sections of the coated tubing were eluted in 10 mL 0.80% $NaNO_3$ at 37° C. with gentle shaking. The resulting fluid was analyzed periodically for silver concentration using a Perkin-Elmer Grafite Furnace Atomic Absorption Spectrometer. The results are given in Table 3:

TABLE 3

| Elution time | Sample A (Zeolite in base coat) | Sample B (Zeolite in top-coat) | Sample C (Zeolite in both coats) | Sample D (High silver level zeolite in base coat) |
|---|---|---|---|---|
| 1 hour | 1.9 ppb | 386 ppb | 461 ppb | 23 ppb |
| 1 day | 5.5 ppb | 416 ppb | 559 ppb | 219 ppb |
| 1 week | 31 ppb | 470 ppb | 606 ppb | 620 ppb |

The results reveal that the silver in the top-coat is most available for exchange with the external medium. In the body, however, such rapidly released silver must be expected to migrate rapidly from the catheter site. In contrast, silver ion from the base coat was barely released from the 5% silver zeolite, Sample A, but showed a sustained release over several days from the 10% silver zeolite, Sample D. Sustained release of silver is preferable to maintain anti-microbial activity at the catheter site. Silver zeolite of high silver content, in the base coat, is clearly preferable for producing sustained silver release. Zeolite containing 5–10% silver is effective, but zeolite containing 10–20% is more preferred.

It should be noted that ability to sustain silver release is obviously also dependent upon the total silver reservoir deposited in a coating. The size of such silver reservoir can be varied, especially increased relative to the Examples above, as is well known in the art, by increasing the thickness of a coating. Coat thickness (independently both top-coat and basecoat) is controlled by varying (increasing or decreasing) the percent solids of the coating solutions, keeping the proportions of the non-solvent components the same. It is also varied, increasing or decreasing, by changing the coating withdrawal speeds. Such changes always entail a balance of factors, however, since the overall characteristics of the coating, such as flexibility, durability and extensibility, for example, may also be altered by changes of coating thickness.

Part Two

In this part, three other bilaminar HYDAK coatings were amended with various silver zeolites, coated onto ethyl vinyl acetate tubing, and examined for silver release.

Tubing samples were cleaned as described in Part One; all coatings were done at 0.20 in/sec withdrawal speed for both base and top-coats. All formulations were agitated for 20 min using a flat bladed mixer before coating. Other coating conditions are given below.

Sample E base coat consisted of HYDAK S103, a solvent-based acrylic copolymer particularly designed for adhesion to silicone substrates. The coating solution consisted of 100 g HYDAK S103 (30% solids), 4 g Des N, 36 g PMA and 110 g of a 20% slurry of Ag10N zeolite AL85H in acetone. The base coat was cured for 40 min at 60° C. The top-coat coating solution consisted of 18.54 g HYDAK A14 (a formulated, crosslinkable solution of hyaluronic acid, prepared according to the method described in U.S. Pat. No. 5,789,571, the disclosure of which is incorporated by reference herein) plus 0.203 g of a 0.20% aqueous solution of Neocryl CX100 trifunctional aziridine crosslinking agent (Neocryl Resins, Inc.). The top-coat was cured for 15 hours at 60° C.

Sample F consisted of an acrylic copolymer aqueous emulsion, HYDAK DC8, a coating noted for its adhesion to metals. The base coat consisted of 22.5 g of DC8 (29% solids), 1.65 g Neocryl CX100 (100% solids), 0.75 g NH$_4$OH (20%), 22.5 g water, and 15 g AgION AK10N-SW20 zeolite suspension (20%). The top-coat was 42 g HYDAK A16 (a formulated, crosslinkable solution of hyaluronic acid, of a type described in U.S. patent application Ser. No. 09/880,476, filed Jun. 12, 2001, the disclosure of which is incorporated by reference) plus 2.10 g of 0.20% aqueous solution of Neocryl CX100. The DC8 base coat was cured for 20 min at 80° C. and the top-coat for 5 hours at 80° C.

Sample G was another acrylic copolymer aqueous emulsion, HYDAK B10195, a general purpose emulsion coating. This sample was prepared exactly as Sample F, substituting the stock HYDAK B10195 for DC8 and eliminating the NH$_4$OH. Curing times, temperatures and top-coat were exactly as for Sample F.

Analysis of silver release involved soaking 1.0-in. segments of the cured coated tubing in 50 mL 0.80% NaNO$_3$ at 37° C. with gentle shaking, and analyzing the silver concentration after 24 hours by atomic absorption. Table 4 gives the results:

TABLE 4

Silver release from various HYDAK coatings

| Sample | Silver after 24 h (ppb) |
|---|---|
| E (S103/A14) | 140 |
| F (DC8/A16) | <1 |
| G (B10195/A16) | 21 |

First, note that these samples were eluted into five times the volume of NaNO$_3$ used in Table 3. Thus, the values for silver concentration in Table 4 must be adjusted (increased) by a factor of 5 to compare them to Table 3. On that basis, silver is most readily released from the S103 base coat, but is probably released too rapidly to sustain an anti-microbial effect. Next best is B10195 aqueous emulsion which appears to offer a sustained release rate, and the least release is from the DC8 system.

To complement these sustained silver releases with an initial burst of anti-microbial soluble silver ion, it was recalled that hyaluronan, a common component of the top-coats of these coatings, is itself a cation exchange medium. Therefore, a charge of soluble silver was applied to samples E–G by briefly soaking the cured coating with 10% AgNO$_3$, rinsing with deionized water, and drying. This process loaded all accessible surface exchange sites with silver. When 1.0-in samples of these materials were analyzed by extraction into 50 mL NaNO$_3$ as for Table 4, the following results were obtained:

TABLE 5

Silver release from top-coat silver-loaded HYDAK coatings

| Sample | Silver after 30 min (ppb) | Silver after 60 min (ppb) | Silver after 24 h (ppb) |
|---|---|---|---|
| E (S103/A14) | 76 | 680 | 870 |
| F (DC8/A16) | 810 | 960 | 1100 |
| G (B10195/A16) | 83 | 740 | 900 |

The results indicate that each of these coatings can provide a source of immediately available silver ion.

It is interesting to note that Sample F, which showed no release of silver from the base coat in 24 hours, showed a distinctly higher capacity to release silver from surface accessible exchange sites. Apparently, other cation exchange sites are available in this coating, relative to the other coatings. These additional sites both increase Sample F's capacity for surface exchange of soluble silver and provide a barrier or sink for silver released from zeolite in the emulsion, delaying or preventing rapid release from the base coat reservoir.

EXAMPLE 3

This Example shows the effectiveness of silver ion as a biocide. To assess the anti-microbial effectiveness of the zeolite-amended coatings, samples were exposed to bacteria and bacterial viability determined. One-foot (12-in.) sections of samples A and B of Example 2, and uncoated ethyl vinyl acetate tubing were separately added to 70 mL of phosphate buffered saline (PBS, 0.90% NaCl plus 10 mM sodium phosphate, pH 7.4). At time zero, 5 mL of a fresh stationary phase broth culture of *S. aureus* (ATCC 25923) was added. The contents were mixed and aliquots plated on nutrient agar to determine the viable count. The mixture was incubated with gentle shaking for 24 hours at 37° C. and re-assayed for viable bacteria. Table 6 shows the results:

TABLE 6

Effect of zeolite coatings on *S. aureus* during 24-h contact

| Sample | CFU/mL, initial | CFU/mL, after 24 h | Reduction (%) |
|---|---|---|---|
| Uncoated control | $4.1 \times 10^5$ | $5.3 \times 10^5$ | No kill |
| A | $4.1 \times 10^5$ | $3.1 \times 10^4$ | 91 |
| B | $4.1 \times 10^5$ | <10* | >99.99 |

*below the limit of detection of the assay

Table 6 shows that the coatings exert an anti-microbial effect. Sample A is most interesting, since it defines an approximate minimal level of silver release that shows anti-microbial activity in these assays. Recall in Table 3 that Sample A only released 5.5 ppb silver after 24 hours incubation, compared to 416 ppb for Sample B. Nevertheless, this sample reduced the *S. aureus* content of this assay by 91%.

The invention thus provides hyaluronan coatings with a compatible source of silver ion that can provide a rapidly released, effective concentration of broad spectrum anti-microbial action supplemented by a substantial, longer acting reservoir of the effective agent available for sustained release during the operating or service life of the structure incorporating the silver ion zeolite-containing hyaluronan coating. Moreover, in such coating, the effective anti-microbial agent concentrates transiently in the surface layer of the coating, where it can be highly effective in preventing surface colonization by pioneer biofilm formers. Further, the anti-microbial agent is supplied in an inherently anti-fouling surface (with respect to the hyaluronan coating).

EXAMPLE 4

This Example shows the effect of zeolite coatings on biofilms. Samples of polyurethane stick (Estane 58284, B. F. Goodrich) nominally 3 mm diameter were coated with the same AgION AL85H-amended base coat composition exactly as described for the Sample D base coat, and top coated with unamended HYDAK A14/CX exactly as described for the Sample E top-coat. These samples were submitted to a flow-cell biofilm assay conducted by Bacterin, Inc., Bozeman Mont. Briefly, in this assay, the coated sticks are placed in a flow-through cell and exposed over a 7-day period to a continuous one-way flow of bacteria (*S. aureus* clinical isolate from a central venous catheter related infection) diluted into sterile defibrinated sheep's blood (BBL Cat # 212391). The study provided 21 such flow-through chambers so that three samples could be taken daily. Samples were assayed for percent coverage of the stick surface by confocal laser scanning microscopy (CLSM) and for viability using the BacLight Live/Dead molecular probe (Molecular Probes, Eugene, Oreg.) and CLSM. Sticks were aseptically scraped, the scrapings sonicated and plated on nutrient agar for viable counts. The results are in Tables 7, 8, and 9.

TABLE 7

*S. aureus* plate counts recovered from the coated stick

| Sample | Day 1 | Day 2 | Day 3 | Day 4 | Day 5 | Day 6 | Day 7 |
|---|---|---|---|---|---|---|---|
| Uncoated | $240 \times 10^3$ | $1.06 \times 10^5$ | $8.00 \times 10^5$ | $6.80 \times 10^5$ | $3.00 \times 10^5$ | $6.50 \times 10^5$ | $4.50 \times 10^5$ |
| Coated | $4.70 \times 10^3$ | $2.20 \times 10^3$ | $2.33 \times 10^3$ | $1.18 \times 10^4$ | $2.30 \times 10^4$ | $3.50 \times 10^4$ | $4.80 \times 10^4$ |

TABLE 8

Percent surface area covered by biofilm

| Sample | Day 1 | Day 2 | Day 3 | Day 4 | Day 5 | Day 6 | Day 7 |
|---|---|---|---|---|---|---|---|
| Uncoated | 45 | 80 | 90 | 95 | 95 | 95 | 95 |
| Coated | 30 | 35 | 30 | 35 | 40 | 40 | 40 |

TABLE 9

Percent of the biofilm that is viable

| Sample | Day 1 | Day 2 | Day 3 | Day 4 | Day 5 | Day 6 | Day 7 |
|---|---|---|---|---|---|---|---|
| Uncoated | 85 | 80 | 90 | 90 | 90 | 90 | 90 |
| Coated | 45 | 50 | 50 | 45 | 55 | 45 | 50 |

The data show that the coated stick resisted biofilm attachment, reduced the overall viable count, and limited the viable cells in the biofilm. The fact that the numbers established by Day 1 were relatively the same over the 7-day period may be explained by the fact that the coated stick had zeolite only in the base coat, and as illustrated in Example 2, Sample D, it requires several hours before an effective level of silver is released. If this sample contained silver exchanged onto surface exchange sites, as further illustrated in Example 2, Sample E, the strong immediate burst of silver may even have reduced the Day 1 levels for the coated sample.

While the invention has been described with respect to various exemplary embodiments, the scope of the invention is not intended to be limited thereby, and variations, modifications and other embodiments of the expressly described features and aspects are readily effected, as will be apparent to the skilled artisan based on the disclosure herein, with all such variations, modifications and other embodiments contemplated as being within the scope of the present invention as hereinafter claimed.

What is claimed is:

1. An article including a surface having a bilaminar, lubricious, and hydrophilic coat thereon, said coating comprising:
   (a) a polysaccharide conponent; and
   (b) an antibiotic ceramic component dispersed within the polysaccharide component,
   wherein the antibiotic ceramic component comprises a zeolite material.

2. An article including a surface having a bilaminar, lubricious, and hydrophilic coating thereon, said coating comprising:
   (a) a polysaccharide component; and
   (b) an antibiotic ceramic component dispersed within the polysaccharide component,
   wherein the polysaccharide component comprises hyaluronan.

3. An article including a surface having a bilaminar, lubricious, and hydrophilic coating thereon, said coating comprising:
   (a) a polysaccharide component; and
   (b) an antibiotic ceramic component dispersed within the polysaccharide component,
   the article comprising a tubing made from a material selected from the group consisting of ethyl vinyl acetate and polyurethane.

4. An article including a surface having a bilaminar, lubricious, and hydrophilic coating thereon, said coating comprising:
   (a) a polysaccharide component; and
   (b) an antibiotic ceramic component dispersed within the polysaccharide component,
   wherein the surface is formed of a material selected from the group consisting of ethyl vinyl acetate and polyurethane.

5. A method for providing an object with antibiotic properties for introduction of the object into an animal, said method comprising:
   coating the object on a surface portion thereof with bilaminar, lubricious, and hydrophilic coating comprising:
   (i) a polysaccharide component; and
   (ii) an antibiotic ceramic component dispersed within the polysaccharide component,
   wherein the polysaccharide component comprises hyaluronan.

6. A method for providing an object with antibiotic properties for introduction of the object into an animal, said method comprising:
   coating the object on a surface portion thereof with bilaminar, lubricious, and hydrophilic coating comprising:
   (i) a polysaccharide component; and
   (ii) an antibiotic ceramic component dispersed within the polysaccharide component,
   wherein the object comprises a tubing made of a material selected from the group consisting of ethyl vinyl acetate and polyurethane.

7. A method for providing an object with antibiotic properties for introduction of the object into an animal, said method comprising:
   coating the object on a surface portion thereof with a bilaminar, lubricious, and hydrophilic coating comprising:
   (i) a polysaccharide component; and
   (ii) an antibiotic ceramic component dispersed within the polysaccharide component,
   wherein the object comprises a material selected from the group consisting of ethyl vinyl acetate and polyurethane.

8. An article comprising a coating, the coating being bilaminar, lubricious, and hydrophilic, the coating containing hyaluronan and a silver ion exchanged zeolite.

9. An article comprising a substrate having a bilaminar coating, the coating including a base coat and a top-coat containing hyaluronan, wherein the base coat contains silver ion exchanged zeolite, and wherein the top coat is lubricious and hydrophilic.

10. A method for providing an object with antibiotic properties for introduction of the object into an animal, said method comprising:
    coating the object on a surface portion thereof with a bilaminar, lubricious, and hydrophilic coating comprising:
    (i) a base coat which adheres firmly to said surface portion, and
    (ii) a hydrophilic, biocompatible top-coat, the top-coat being chemically grafted to said base coat, the top-coat including a polysaccharide component,
    the method further comprising dispersing an antibiotic ceramic component within said base coat.

11. The method of claim 10, wherein the antibiotic ceramic component comprises a zeolite component.

12. The method of claim 10, wherein the zeolite component comprises silver ions ion-exchanged thereon.

13. The method of claim 10, wherein the polysaccharide component comprises hyaluronan.

14. The method of claim 10, wherein the object comprises polymeric tubing.

15. The method of claim 10, wherein the object comprises polymeric catheter tubing.

16. The method of claim 10, wherein the object comprises a tubing made of a material selected from the group consisting of ethyl vinyl acetate and polyurethane.

17. The method of claim 10, wherein the object comprises a polymeric material.

18. The method of claim 10, wherein the object comprises a material selected from the group consisting of ethyl vinyl acetate and polyurethane.

19. An article having a bilaminar, lubricious, and hydrophilic coating which includes a polysaccharide and silver ion exchanged zeolite.

20. An article having a bilaminar, lubricious, and hydrophilic coating which includes hyaluronan and a silver ion exchanged zeolite.

* * * * *